United States Patent [19]

Marsoner et al.

[11] Patent Number: 4,705,667
[45] Date of Patent: Nov. 10, 1987

[54] ANALYZING APPARATUS FOR MEASURING LIQUID OR GASEOUS SAMPLES

[75] Inventors: Hermann Marsoner, Steinberg; Erich Kleinhappl, Kumberg, both of Austria

[73] Assignee: AVL AG, Schaffhausen, Switzerland

[21] Appl. No.: 695,066

[22] Filed: Jan. 25, 1985

[30] Foreign Application Priority Data

Feb. 2, 1984 [AT] Austria .................................. 341/84

[51] Int. Cl.⁴ ..................... G01N 1/02; G01N 1/14; B65B 3/04; B65B 3/14
[52] U.S. Cl. ........................................ 422/68; 422/80; 73/864.21; 73/864.24; 73/864.25; 73/864.81; 141/31; 141/65; 141/130
[58] Field of Search .................... 422/68, 80; 141/31, 141/65, 130; 73/864.21, 864.24, 864.25, 864.81

[56] References Cited

U.S. PATENT DOCUMENTS

| | | | |
|---|---|---|---|
| 2,877,611 | 3/1959 | Anrep | 141/31 X |
| 3,561,273 | 2/1971 | Tanila | 73/863.23 X |
| 4,338,280 | 7/1982 | Ambers et al. | 422/68 |
| 4,499,053 | 2/1985 | Jones | 422/68 |

FOREIGN PATENT DOCUMENTS

| | | | |
|---|---|---|---|
| 2805137 | 8/1979 | Fed. Rep. of Germany | 73/864.21 |
| 1465678 | 2/1977 | United Kingdom | 73/864.25 |

Primary Examiner—Michael S. Marcus
Assistant Examiner—Lynn M. Kummert
Attorney, Agent, or Firm—Watson, Cole, Grindle & Watson

[57] ABSTRACT

In its initial position an input opening of a sample input device provides a seal against a funnel element which is directly connected to a feed pipe delivering standard media and to a valve-controlled air supply, and which has a feed opening cooperating with the input opening. Thus, in the initial position of the sample input device, the input opening and the feed opening at the funnel element together are part of a closed path for the additional media required for measurement and cleaning purposes, which will simplify the overall design of the apparatus.

6 Claims, 6 Drawing Figures

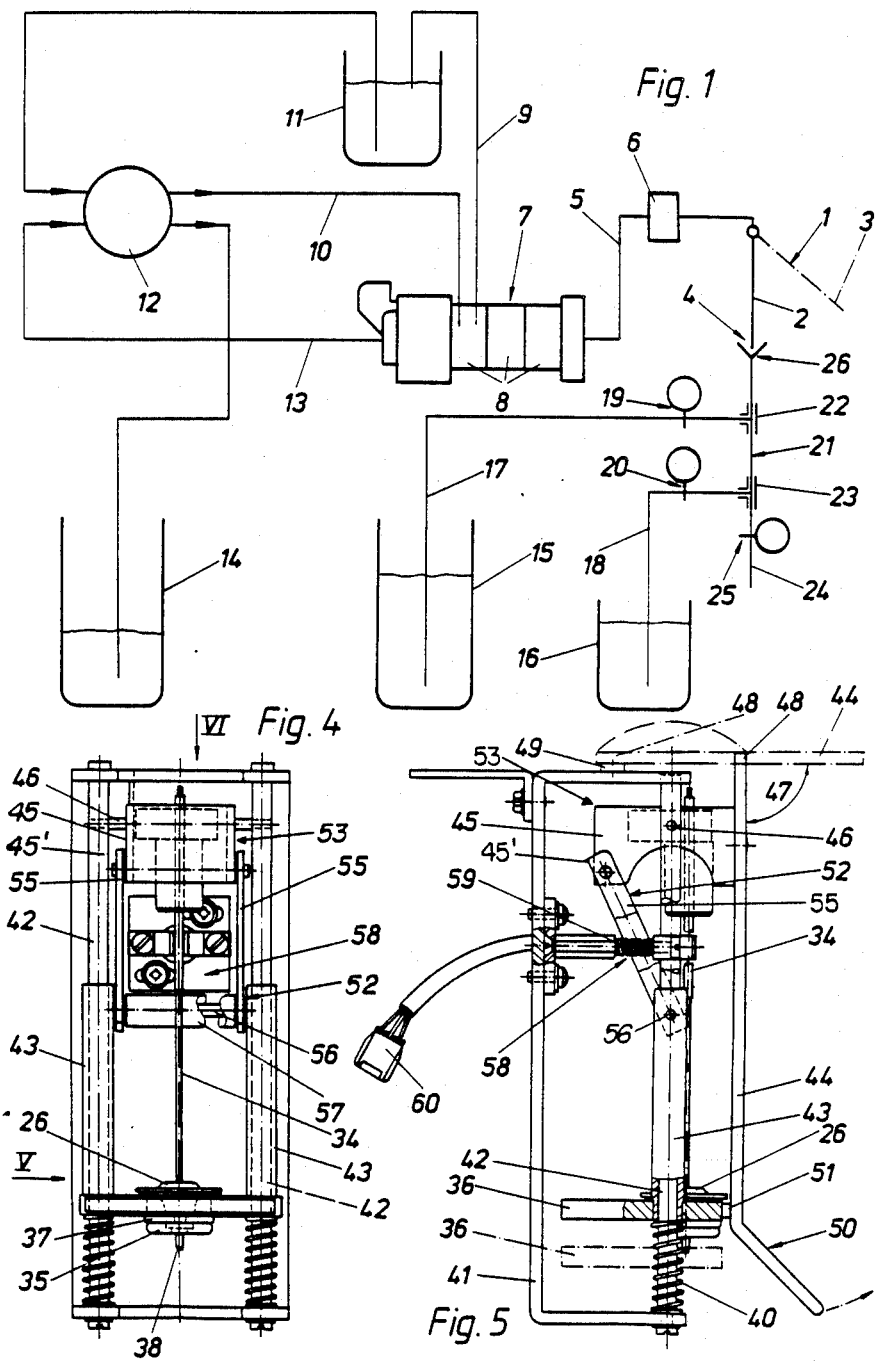

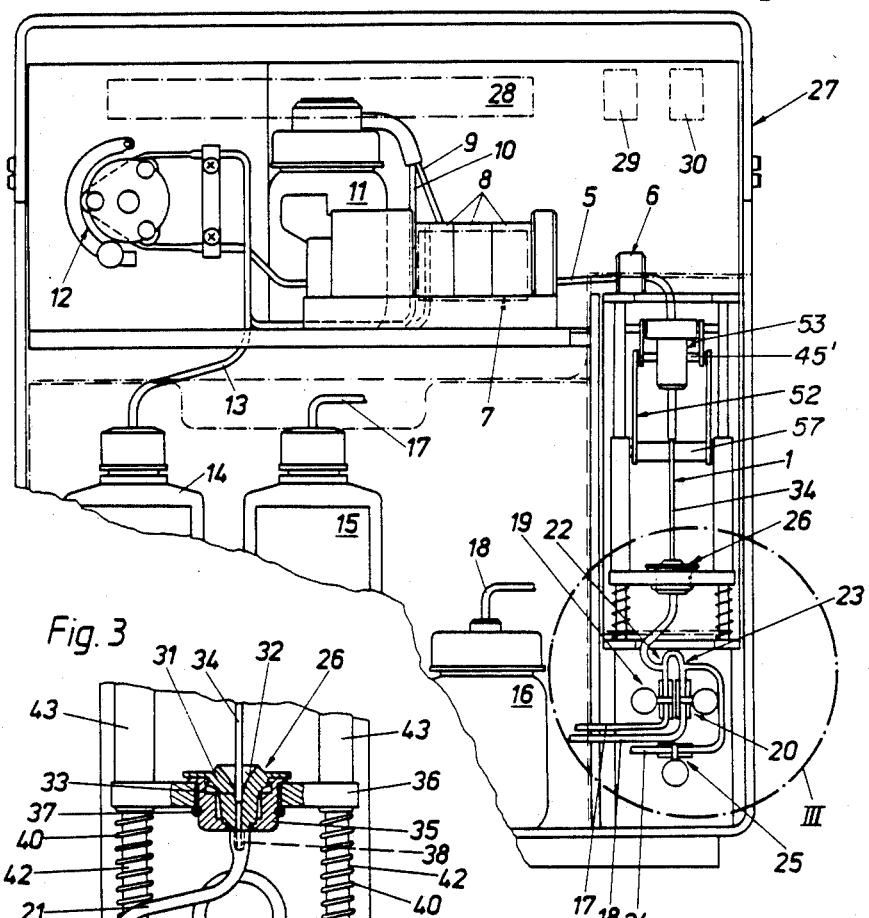
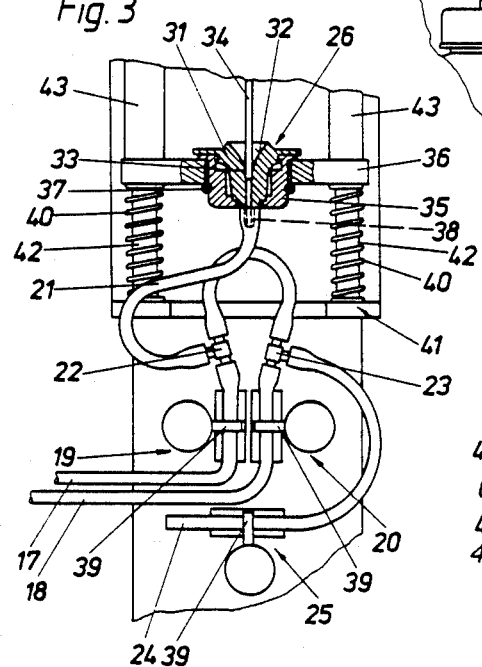
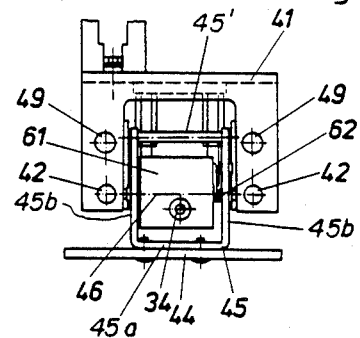

ANALYZING APPARATUS FOR MEASURING LIQUID OR GASEOUS SAMPLES

BACKGROUND OF THE INVENTION

This invention relates to an analyzing apparatus for measuring liquid or gaseous samples, comprising a sample input device with an input opening for introducing a sample into the path of analysis, which opening may be actuated to move relative to the analyzer from an initial position to a feed position, and further comprising one or more measuring chambers, a feed pump and a waste vessel, all of which are connected via hose pipes, and further comprising additional hose pipes for the delivery of standard media that may be introduced into the path of analysis by means of valves.

DESCRIPTION OF THE PRIOR ART

Such analyzers have been described before, for instance in German laid-open print 25 21 061, and for example are used for analyzing blood and other biological liquids. The sample enters the path of analysis by an input opening which may be actuated to move relative to the analyzer from an initial position to a feed position by means of a positioning mechanism, in which feed position the samples delivered for analysis in sample vessels, etc., may be taken in via the input opening. In the initial position for this known type of device the input opening is coupled to a cleaning device dispensing liquid and gaseous media for cleaning and drying the input opening and the path of analysis behind it.

The main disadvantage of this known type of analyzer, the great complexity of design necessitated by the feed of standard and calibrating media, cleansing liquids, reagents and other such substances required for measurement purposes, since the individual media are introduced into the sample or analysis path at different points, which will require a considerable number of additional branch-off and shut-off devices, together with the necessary actuating and control elements.

SUMMARY OF THE INVENTION

It is an object of the present invention to modify an analyzing apparatus of the above type such that the necessary standard and cleansing solutions, etc., may be introduced in a simpler manner, resulting in an uncomplicated overall design of the apparatus and offering greater ease of operation and maintenance in addition to being less costly.

According to the present invention this is achieved by configuring the apparatus such that in its initial position the input opening of the sample input device will come into sealing contact with the outlet opening of a flow channel through a funnel element, the flow channel having an inlet opening which is connected to further hose pipes for delivering standard media and air thereto. This set-up will ensure that in its initial position the input opening of the sample input device, together with the outlet opening of the flow channel through the funnel element, will form part of a closed path for the additional media required for measuring and cleaning, this closed path being interrupted only during the actual sample intake by actuating the input opening to move relative to the analyzer from its initial position to its feed position. Passage of the individual media through the sample path is identical, i.e., at least between the input opening and the waste vessel, which will considerably simplify control of the flow of liquids to be introduced into the path of analysis, shut-off valves, etc., for instance, are necessary in front of the fittings of the funnel element only, and will greatly facilitate repair and maintenance. The greater simplicity of the overall design will reduce both outer dimensions and weight as well as manufacturing costs.

In an analyzer whose sample input device is configured as a hollow needle that may be tilted into feed position, the input opening being placed at its point, and which is provided with a tilting mechanism producing a relative movement in the direction of the needle axis at the beginning of the tilting phase in order to remove the point of the needle from the initial position, as has been described in the above German laid-open print 25 21 061, for example, a further embodiment of the present invention provides that in the initial position the point of the hollow needle establishes a direct sealing contact with the outlet opening of flow channel through the funnel element.

The above publication essentially describes a cleaning device for an analyzing apparatus in which the hollow needle used for sample input will dip in its untilted, i.e., initial, position relative to the analyzer, into a vessel containing a cleansing fluid whose fluid level relative to the dipped needle is kept approximately constant. As mentioned before, in this known kind of apparatus any other media required for measuring and calibrating are entered via additional facilities adding to the complexity of design.

According to the above proposal a perfect seal is achieved in a simple manner between the input opening located at the point of the hollow needle and the outlet opening of the funnel element, regardless of any inaccuracies in the positioning of the two openings relative to each other due to maintenance and manufacturing tolerances.

In another preferred embodiment of the present invention a spring-loaded actuator flap is provided as part of a housing which will act as a cover of the sample input device whenever the hollow needle is in its initial position, and which is connected via a lever mechanism to the funnel element guided in the direction of the hollow needle axis, and which flap will therefore push the funnel element away from the point of the hollow needle whenever it is lifted from its initial position, and which is further connected to a tilting lever provided with a cross-element which in the initial position is at a certain distance from the hollow needle, such that this cross-element will be in contact with the hollow needle approaching it from inside the analyzing apparatus once a given lifting angle of the actuator flap has been reached. If the actuator flap is lifted any further, this cross-element will carry along with it the hollow needle which may be rotated around a shaft fixed in the housing, until the feed position has been reached. The actuator flap ensures protection of the sensitive components of the sample input device during operation of the apparatus. Lifting of the actuator flap will permit access to the sample input device from outside for the purpose of sample intake, in addition to effecting a tilting of the hollow needle with the input opening at its end. For this purpose the funnel element guided in the direction of the axis of the hollow needle is moved away from the point of the hollow needle, thus releasing the hollow needle and allowing it to tilt. Since both actions are caused by the same lifting of the actuator flap, it may be ensured in a simple manner that the hollow needle will only begin to tilt after the actuator flap has reached a lifting angle at which the funnel is no longer in contact with the point of the hollow needle. After the sample has been fed into the input opening at the point of the tilted hollow needle, the actuator flap is closed again, which will first cause the hollow needle to tilt back into its initial position, upon which the funnel guided in the direction of the hollow needle axis, is moved back towards the point of the hollow needle. Once the input opening of the hollow needle is sealed tightly against the outlet opening of the funnel element, the sample intake is completed and other media may be introduced via the funnel.

According to still another embodiment of the invention the lever mechanism is configured as a two-part articulated lever, and springs are provided between the funnel element and a supporting part fixed in the housing for loading the actuator flap, causing it to be arrested either in initial or feed position after a threshold point of the articulated lever has been passed. In this way the actuator flap and thus the hollow needle with the input opening, will remain in their respective position, i.e., feed position or initial position, as long as no tilt into the respective other position is initiated, for instance, by the operator of the analyzer.

DESCRIPTION OF THE DRAWINGS

The present invention will now be further illustrated, by way of example only, with reference to the accompanying drawings in which FIG. 1 is a diagrammatic view of an analyzing apparatus according to the invention;

FIG. 2 presents a front view of an apparatus as in FIG. 1, with the cover removed;

FIG. 3 shows detail III of FIG. 2;

FIG. 4 presents a front view of a sample input device for an apparatus as shown in FIG. 2;

FIG. 5 shows a view along arrow V in FIG. 4;

FIG. 6 shows a view along arrow VI in FIG. 4.

DESCRIPTION OF THE PREFERRED EMBODIMENT

FIG. 1 presents an analyzing apparatus for measuring liquid or gaseous samples, comprising a sample input device 1 with an input opening 4 for introducing a sample into the path of analysis, which opening may be actuated to move relative to the analyzer from an initial position 2 to a feed position 3. The sample input device, which in this example is configured as a tiltable hollow needle, is connected to a measuring chamber 7 by means of a hose pipe 5 into which a photoelectric sensor 6 has been incorporated in order to monitor the passage of the sample or standard medium. In this instance the measuring chamber 7 consists of three measuring cells 8 receiving the sample flow which are interconnected by central capillary bores (not shown here). The measuring cells may be designed for a large variety of substances and ions, and are configured in accordance with the measurement task given, delivering for evaluation measuring signals of a size proportional to the quantity to be analyzed, via signal leads that are not shown in this drawing. In the variant according to FIG. 1 the left one of the three measuring cells 8 is a reference cell into which a reference solution (e.g., KCl) may be fed from a reference solution vessel 11 via hose pipes 9, 10. A hose pump 12 serves for circulation of the reference solution through hose pipes 9, 10 as well as for drawing off the respective media delivered to the measuring chamber 7 via hose pipe 5, by means of hose pipe 13 discharging into a waste vessel 14 behind the hose pump 12.

In addition to the reference solution vessel 11 and the waste vessel 14, two other vessels 15, 16 are provided which are arranged such that they may be replaced, like the two vessels mentioned before, and which may contain different standard solutions, reagents, etc., and which are connected via hose pipes 17, 18 with elements 22, 23 opening into a feed pipe 21. One end of the feed pipe 21 carries a fitting 24 for drawing in air; fitting 24 and the hose pipes 17,18 can be closed by valves 19,20,25.

On its other end, i.e., the one opposite of the air supply fitting 24, the feed pipe 21 is connected with a funnel element 26 which is sealed by the input opening 4 of the sample input device 1 in its initial position 2, and which has a flow channel therethrough that defines an outlet opening (not shown here) cooperating with the input opening 4.

Permitting the standard or cleansing media as well as a quantity of air for separation of the individual batches and for drying the sample path to be entered through the input opening of the sample input device in its initial position relative to the analyzer, will ensure a simple design of the apparatus, eliminating the need for any valves or other shut-off devices in the actual path of analysis to be travelled by the sample. Only during sample intake must the tight seal between input opening 4 and the funnel 26 be broken and the sample input device must be tilted in order to pick up the sample at the input opening; in all other operational states of the apparatus the media path between the feed vessels 15,16 and the waste vessel 14 is a closed circuit, the medium actually entered into the path of analysis being controlled via the three valves 19,20,25 only.

The photoelectric sensor 6 will help to recognize whether the quantity of sample passing through the input opening 4 during sample intake is sufficient for measurement, whether passage of the sample through the measuring chamber has been completed, etc.

The variant detailed in FIG. 2 essentially corresponds to the diagram of FIG. 1; corresponding parts are identified by the same reference numbers in both drawings; in order to avoid repetitions the reader is referred to the descriptions of parts and functions given for FIG. 1.

In addition to the parts corresponding to those in FIG. 1, FIG. 2 shows an analyzer housing 27 whose design details are of little relevance in this context as they are largely determined by the space-saving arrangement of the above parts. Typically, the housing is closed all around, and any openings required for maintenance purposes are provided with easily detachable covers; such openings are provided primarily in the vicinity of the vessels 11,14,15,16 and the above valves and hose pipes. The evaluation unit for the signals delivered by the measuring chamber 7, as well as the power supply and the controls for the valves 19,20,25, the photoelectric sensor 6 and the hose pump 12 may be located on the rear side of the apparatus in the housing 27, for instance; they are not shown in this drawing. A display panel 28 and two push-button controls 29,30 are indicated by dot-dash lines.

In the lower right-hand corner of the housing 27 of the apparatus shown in FIG. 2 the funnel element 26 of the sample input device 1, as well as its fittings, are presented; the special design of these parts will be discussed below, with reference to FIGS. 3 to 6.

FIG. 3, which is an enlarged section of detail III in FIG. 2, shows the funnel element 26 whose inner part 31, made of some plastic material, has a flow channel therethrough which defines a funnel-shaped outlet opening 32 which is sealingly contacted by the point 33 of the hollow needle 34 if the sample input device is in the initial position shown. The inner part 31 of the funnel element 26 is held in a fitting 35 which is inserted into an opening of a carrier plate 36 and fastened by a ring 37.

The opposite end of the flow channel in the funnel element 26 defines an inlet opening within a nipple 38 to which the feed pipe 21 is connected. Besides, via orifices 22,23 configured as T-elements, the feed pipe 21 is connected to the hose pipes 17,18 leading to the vessels containing the standard media, for example, in a manner not shown here, and to fitting 24 for the supply of outside air.

The valves 19,20,25 are pinch valves in this variant, permitting the hoses running in suitable guides to be squeezed shut by means of pin bolts 39 actuated by lifting magnets or similar such devices.

The carrier plate 36 carrying the funnel element 26 is supported by springs 40 relative to a supporting part 41 fixed in the housing, and may be pushed away from the hollow needle 34 in the direction of the needle axis against the force of the springs 40, by means of two guiding sleeves 43 sliding along guide rods 42. Further details of the shifting mechanism will be discussed below (cf. FIGS. 4 to 6).

With regard to FIG. 3, it should be noted that only one of the valves 19,20,25 will be open if the hollow needle 34 is in the initial position of the sample input device (as shown), and that the medium entering the input opening 4 located in the point 33 of the hollow needle 34 is permitted to flow in only from one of the hose pipes 17,18 or from fitting 24.

FIG. 4 presents the sample input device in its initial position, with the actuator flap 44 shown in FIGS. 5 and 6 removed for the sake of clarity. With its point the hollow needle 34 is in sealing contact with the outlet opening of the flow channel through the funnel element 26 described above (cf. FIG. 3); at the bottom of the funnel the nipple 38 is shown which provides a connection for the feed pipe (not indicated here). The remaining parts presented in FIGS. 4 to 6 and mentioned before in the description of the drawings, again have their former reference numbers.

In FIG. 5 the actuator flap 44, which may be made from moulded plastic, forms part of the housing of the analyzer (not shown here) in the initial position of the sample input device, covering the whole area of the sample input device. At its upper end the actuator flap 44 is connected to a tilting lever 53. This tilting lever includes a generally U-shaped swivel bracket 45 which includes a base 45a to which the actuator flap is connected and two arms 45b. It also includes a shaft 46 which extends through the arms 45b and is fixed at its opposite ends in the respective guide rods 42 of the supporting part 41, and a cross axle 45' which extends through the arms 45b near their free ends. The swivel bracket 45 is rotatable about shaft 46 when the actuator flap 44 is tilted away from the front face of the analyzer by an angle 47 (e.g., 90°). In the tilted position of the actuator flap 44 (indicated by a dash-dot line) its upper end 48 will rest against a stop 49 (made from some elastic material, for instance) which is attached to the housing. The lower end 50 of the actuator flap 44 has a slight upward bend to facilitate handling; in the initial position the lower end 50 rests against a stop 51 on the carrier plate 36, which stop again may be made from some elastic material.

Attached to the cross axle 45' of the bracket 45 are the upper ends of arms 55 of a lever mechanism 52. The lever mechanism 52 also includes a cross element 56 which is connected between the lower ends of the arms 55 and through aligned openings in the guiding sleeves 43. The tilting lever 53 and lever mechanism 52 together provide a two-part articulated lever system. When the actuator flap 44 is tilted upwardly, this causes the swivel bracket 45 to rotate about shaft 46, which in turn causes the cross axle 45' to initially move along a circular arc (toward the carrier plate 36). As a result, the arms 55 of lever mechanism 52 are moved downwardly, causing the guide sleeves 43 to slide downwardly along the guide rods 42 (in parallel with the central axis of the hollow needle 34), thus lowering the carrier plate 36 and compressing the springs 40. The carrier plate 36 will assume the position shown in dash-dot lines in FIG. 5. In this manner the funnel element 26 is moved away from the point of the hollow needle 34 when the lower end 50 of the actuator flap 44 is lifted.

Once a given tilting angle of the actuator flap 44 has been reached, the cross axle 45', due to the continued rotation of the swivel bracket 45 around the fixed shaft 46, will contact the hollow needle 34 from within the analyzing apparatus, carrying it along if the actuator flap 44 is lifted any further until the feed position (not shown in this drawing) has been reached. As is seen in FIG. 4, the cross-element 56 of the lever mechanism 52 is provided with an elastic cover 57 in order to protect the needle when the needle is in its initial position. The configuration of the tilting lever 53 and its cooperation with the hollow needle 34 may also be seen in FIG. 2.

Furthermore, FIGS. 4 and 5 show the positioning of a photoelectric sensor 58 which is mounted on part 41 fixed within the analyzer housing by screws 59, and may be adjusted to the initial position of the hollow needle 34, and which will provide, via a connecting plug 60, information on the particular position of the needle to the evaluation and control unit of the analyzer (not shown here).

Due to the configuration and design of the swivel bracket 45 and the linkage of the two levers 52, cooperation with the springs 40 will ensure that the actuator flap 44 will be arrested either in the initial position indicated by a full line, or in the feed position indicated by a dot-dash line, after a threshold point has been passed, and will remain there until movement towards the other position is initiated by the operator.

FIG. 6 shows that the upper end of the hollow needle 34 is held in a needle support block 61 which also rotates around the shaft 46 between the arms 45b of the swivel bracket 45 and is carried into feed position by the tilting lever 53 (cf. FIG. 4) when the actuator flap 44 is lifted. Continuous contact between the hollow needle 34 and the elastic cover 57, or cross-element 56 of the tilting lever 53, is ensured by a spring 62 between the swivel bracket 45 and the needle support block 61.

We claim:

1. An analyzing apparatus for analyzing liquid or gaseous samples which comprises
   a sample input device including a movable hollow input needle which defines a central axis and has a point end in which an input opening is located, and a tilting mechanism to move said hollow input needle between a first position for obtaining a sample for analysis and a second position for introducing standard media or air into said hollow input needle, a sample measuring cell for analyzing liquid or gaseous samples, said sample measuring cell having an input side and an output side, said sample input device being connected to the input side of said measuring cell, a feed pump which is connected to the output side of said sample measuring cell for drawing liquid or gaseous samples from said hollow input needle to said sample measuring cell and discharging the same to a waste vessel, a funnel element having a conical portion and a flow channel therethrough, said flow channel having an inlet opening and an outlet opening, said outlet opening being connected directly to a smaller end of said conical portion, said funnel element being positioned relative to said sample input device such that, when the hollow input needle of said sample input device is moved to its second position, it will be in sealing contact with said smaller end of said conical portion adjacent to said outlet opening of said flow channel of said funnel element, a first hose pipe connected to the inlet opening of said flow channel in said funnel element, a valved second hose pipe connected to said first hose pipe to supply air thereto, and a valved third hose pipe connected to said first hose pipe to supply said standard media thereto, said tilting mechanism comprising a spring-loaded actuator flap which acts as a cover of said sample input device whenever said hollow input needle is in said second position, a tilting lever comprising a swivel bracket which is connected to said actuator flap, and a lever mechanism which includes arms connecting said funnel element to said swivel bracket to guide said funnel element in the direction of the central axis of said hollow input needle, said arms acting to push said funnel element away from said point of said hollow input needle whenever said actuator flap is lifted from its initial position, said tilting lever being provided with a cross axle which, in said second position of said hollow input needle, is at a certain distance from said hollow input needle, such that said cross axle will be in contact with said hollow input needle once a given lifting angle of said actuator flap has been reached, and that, upon said actuator flap being lifted further, said cross axle will carry along with it said hollow input needle, which can be moved around a fixed shaft in said apparatus until said first position has been reached.

2. An analyzing apparatus as defined in claim 1, wherein said lever mechanism and said tilting lever provide a two-part articulated lever system, wherein said sample input device includes a fixed supporting part, and wherein springs are provided between said funnel element and said fixed supporting part for loading said actuator flap, causing it to be arrested in one of said two positions after a threshold point of said articulated lever system has been passed.

3. An analyzing apparatus as defined in claim 1, including a first vessel for containing a first standard media, and wherein said valved third hose pipe is connected between said first vessel and said first hose pipe.

4. An analyzing apparatus as defined in claim 3, including a second vessel for containing a second standard media, and a valved fourth hose pipe connected between said second vessel and said first hose pipe.

5. An analyzing apparatus as defined in claim 1, wherein said sample input device includes a supporting part having two parallel guide rods which extend in parallel with the central axis of said hollow input needle when said hollow input needle is in said second position; wherein said sample input device includes a carrier plate which supports said funnel element and is mounted to be movable along said parallel guide rods; wherein said tilting lever includes a shaft which extends between said guide rods; wherein said swivel bracket is rotatably mounted around said shaft and supports a cross axle; wherein said actuator flap has an upper end which is connected to said swivel bracket and a lower end, wherein lifting of said lower end causes said swivel bracket, when said hollow input needle is in its second position with its said one end located within said funnel element, to rotate about said shaft such that said cross axle will move in a circular arc toward said carrier plate; wherein said lever mechanism includes a cross element which is connected to move said carrier plate along said parallel guide rods, and wherein said arms of said lever mechanism are connected between respective opposite ends of said cross element and said cross axle, such that initial lifting of the lower end of said actuator flap will cause said swivel bracket to rotate about the shaft, thus causing said lever mechanism to move said carrier plate and thus the funnel element away from said one end of said hollow input needle, and after a certain additional lifting of the lower end of said actuator flap, causing said cross axle to contact said hollow input needle along its length and rotate said hollow input needle to said first position thereof.

6. An analyzing apparatus as defined in claim 5, wherein said swivel bracket is generally U-shaped and has a base and two arms, wherein said shaft extends through said arms, and including a needle support block mounted on said shaft between said arms, said hollow input needle being mounted in said needle support block.

* * * * *